US006919450B2

(12) United States Patent
Thaper et al.

(10) Patent No.: US 6,919,450 B2
(45) Date of Patent: Jul. 19, 2005

(54) PROCESS FOR THE PREPARATION OF BENAZEPRIL

(75) Inventors: Rajest Kumar Thaper, Jammu and Kashmir (IN); Yatendra Kumar, Haryana (IN); Shantanu De, Delhi (IN); S.M. Dileep Kumar, Vizianagaram (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/472,811

(22) PCT Filed: Mar. 14, 2002

(86) PCT No.: PCT/IB02/00764

§ 371 (c)(1),
(2), (4) Date: Mar. 30, 2004

(87) PCT Pub. No.: WO02/076375

PCT Pub. Date: Oct. 3, 2002

(65) Prior Publication Data

US 2004/0152889 A1 Aug. 5, 2004

(30) Foreign Application Priority Data

Mar. 27, 2001 (IN) ..................................... 374/DEL/2001

(51) Int. Cl.$^7$ .................... C07D 487/00; C07D 491/00; C07D 498/00; C07D 513/00
(52) U.S. Cl. ..................................................... 540/523
(58) Field of Search ............................ 540/523; 558/52

(56) References Cited

U.S. PATENT DOCUMENTS

| 4,410,520 A | 10/1983 | Watthey | ...................... 424/244 |
| 4,785,089 A | 11/1988 | Blaser et al. | ................ 540/523 |

FOREIGN PATENT DOCUMENTS

| CA | 1267903 | 4/1990 | .............. 260/319.3 |
| CA | 1292236 | 11/1991 | .............. 260/387.1 |
| CA | 1332943 | 11/1994 | .............. 260/238.6 |
| EP | 0 072 352 | 8/1982 | ......... C07D/223/16 |

OTHER PUBLICATIONS

Urbach & Henning, "A Favourable Diastereoselective Synthesis of N− (1−S−Ethoxycarbonyl−3−Phenylpropyl) −S−Alanine", *Tetrahedron Letters*, 25(11): 1143–1146 (1984).

Peter J. Stang et al., "Single−Step Improved Synthesis of Primary and Other Vinyl Trifluoromethanesulfonates", Synthesis, 283–284 (1980).

A. Garcia Martinez et al, "Sterically Hindered Bases. Synthesis of 2,4,6−Trisubstituted Pyrimidines", Synthesis, 881–882 (Oct. 1990).

*Primary Examiner*—James O. Wilson
*Assistant Examiner*—Zachary C. Tucker
(74) *Attorney, Agent, or Firm*—Jayadeep R. Deshmukh, Esq.

(57) ABSTRACT

The present invention relates to an improved process for the preparation of trifluoromethanesulfonic ester of ethyl (R)-2-hydroxy-4-phenylbutyrate, referred to here as triflate in structural Formula I, and to the use of this compound as intermediate for the preparation of ACE (Angiotensin Converting Enzyme) inhibitor, benazepril.

4 Claims, No Drawings

PROCESS FOR THE PREPARATION OF BENAZEPRIL

This application was filed under 35 U.S.C. 371, and is the U.S. National Stage of PCT/IB2002/000764, which application was filed 14 Mar. 2002.

FIELD OF THE INVENTION

The present invention relates to an improved process for the preparation of trifluoromethanesulfonic ester of ethyl (R)-2-hydroxy-4-phenylbutyrate, referred to here as triflate of the following structural Formula I,

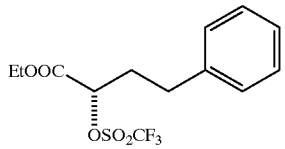

FORMULA I and to the use of this compound as intermediate for the preparation of ACE (Angiotensin Converting Enzyme) inhibitor, benazepril.

BACKGROUND OF THE INVENTION

Chemically, benazepril is (3S)-1-(carboxymethyl-[[(1S)-1-(ethoxycarbony)-3-phenylpropyl]amino]-2,3,4,5-tetrahydro-1H-[1]benzazepin-2-one of Formula II.

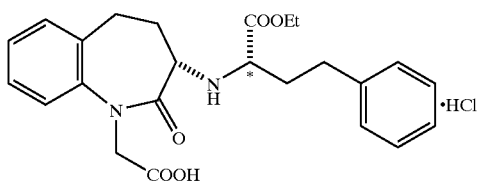

FORMULA II

Benazepril is a well-known long acting ACE inhibitor primarily for the treatment of hypertension and was reported for the first time in U.S. Pat. No. 4,410,520.

Benazepril and other ACE inhibitors can be prepared by reacting an appropriate ester of (R)-2-hydroxy-4-phenylbutyric acid with an appropriate amine under standard conditions well known in the art. For example, Urbach and Henning, Tetrahedron Left, 25, 1143 (1984), discloses a synthesis using trifluoromethanesulfonic ester of ethyl (R)-2-hydroxy-4-phenylbutyrate.

In Canadian Patent Nos. 1292236 and 1267903 is disclosed a process for preparing the triflate of Formula I. The method comprises reacting an α hydroxycarboxylic acid derivative with a trifluromethanesulfonating agent in an inert solvent such as methylene chloride in the presence of a base such as pyridine to afford the triflate of Formula I in 84.3% yield. The triflate prepared by the above method when used in the synthesis of benazepril in the laboratory does not give the desired yields of benazepril hydrochloride. In fact, a low overall yield of 46% of benazepril hydrochloride was obtained which is not acceptable at a commercial scale. The low yield is attributable to the formation of pyridinium salt, when trifluoromethanesulfonic anhydride and pyridine are combined.

To overcome the problem of the formation of pyridinium salts during triflate formation, pyridine was replaced with sterically hindered bases such as 2,6-di-tert-butyl-4-methylpyridine and 2,4,6-tri-substituted pyrimidines (for example, Peter J. Stang et al, Synthesis, 1980, p-283; A-Garcia Martinez et al, bid, 1990, p-881). The use of these bases is not practical on a commercial scale owing to the high cost involved.

In U.S. Pat. No. 4,785,089, it has been emphasized that aromatic p-nitro or halo sulfonic esters of ethyl (R)-2-hydroxy-4-phenylbutyrate give better results than the trifluoromethane sulfonic ester of ethyl (R)-2-hydroxy-4-phenylbutyrate when used in the synthesis of ACE inhibitors like benazepril. The process involves alkylation of benzo-fused lactam with p-nitro or halo sulfonic ester of (R)-2-hydroxy-4-phenylbutyrate at 75–80° C. for about 9 hours and results in an overall yield of benazepril hydrochloride as 83.5%. However, this process is also not completely satisfactory and is disadvantageous at a commercial scale because of low overall yield.

It is, therefore, desirable to solve the problems associated with the prior art and to provide an efficient process for the preparation and isolation of the triflate of Formula I which process improves the economics by resulting in higher yields of benazepril hydrochloride and less reaction time. The process is easy to handle at commercial scale and causes the removal of the excess pyridine and pyridinum salts without any difficulty.

SUMMARY OF THE INVENTION

It is an object of the present invention to provide a process for preparing trifluoromethanesulfonic ester of ethyl (R)-2-hydroxy-4-phenyl butyrate of Formula I, which comprises reacting ethyl (R)-2-hydroxy-4-phenyl butyrate of Formula III,

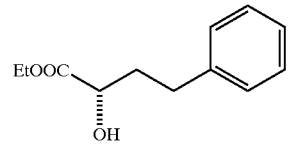

FORMULA III with trifluoromethanesulphonic anhydride of Formula IV,

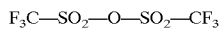

FORMULA IV in an inert solvent in the presence of a base and purifying it by passing through a column.

The base used to trap the acid formed during the course of the reaction may be selected from inorganic or organic bases. The inorganic base is selected from potassium carbonate, sodium carbonate or sodium bicarbonate and the organic base is selected from triethylamine or pyridine. Most preferably, pyridine is used.

The term 'inert solvent' includes solvents which cannot react with the trifluoromethane sulfonating agent and the trifluoromethanesulfonating acid derivatives. Solvents used include halogenated hydrocarbons such as methylene chloride, chloroform, carbon tetrachloride and aromatic hydrocarbons such as toluene, benzene or hexane. Most preferably, methylene chloride is used.

The reaction is carried out within the temperature range from about −80° C. to +80° C., preferably between −80° C. to room temperature.

In another aspect, the triflate of Formula I prepared by the process of the present invention is condensed with 3-amino benzofused lactam, namely 1-tert.-butoxycarbonylmethyl-3-S-amino-2,3,4,5-tetrahydro-1H-(1)-benzazepin-2-one of structural Formula V,

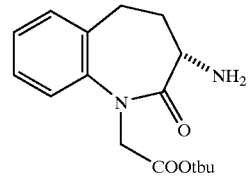

FORMULA V in the presence of a solvent, e.g., in the presence of a chlorinated lower alkane such as chloroform or methylene chloride and an acid acceptor, e.g., an inorganic base such as a bicarbonate, carbonate or hydroxide of an alkali metal, an organic quaternary ammonium salt, e.g. a letrabubylammonium salt, or an organic tertiary base such as triethylamine, N-ethyl piperidine, N-methylmorpholine, pyridine or quinoline at a temperature from about 0 to 50° C. for about 2 to 5 hours followed by a suitable work-up which gives the hydrochloride salt of benazepril. The starting compound, 1-tert.-butoxycarboxylmethyl-3-S-amino-2,3,4,5-tetrahydro-1H-(1)-benazepin-2-one of structural formula V is known and can be prepared by the method disclosed in European patent application No. 72352.

DETAILED DESCRIPTION OF THE INVENTION

In the following section preferred embodiments are described by way of examples to illustrate the process of this invention. However, these are not intended in any way to limit the scope of the present invention.

EXAMPLE 1

Preparation of (3S)-1-(carboxymethyl-[[(1S)-1-(ethoxycarbonyl)-3-phenylpropyl]amino]-2,3,4,5-tetrahydro-1H-[1]benzazepin-2-one Hydrochloride Salt 5.67 g of ethyl (R)-2-hydroxy-4-phenyl butyrate (99% ee), 2.79 g of pyridine were taken up in methylene chloride and cooled to −20° C. A solution of 10 g of trifluoromethane sulphonic anhydride in methylene chloride was added during 15–20 min. The reaction mixture was then stirred for 30 minutes at −20 to −25° C. and monitored by TLC. After the completion of the reaction, the mixture was directly passed through a column of silica gel, (25 g, 60–125 mesh, 1 inch diameter column) using methylene chloride as eluent. The fractions were combined and solvent removed to afford ethyl(R)-2-(trifluoromethane sulphonyloxy)-4-phenyl butyrate (triflate) as an oil. The oil was dissolved in 15 ml methylene chloride and added dropwise to a mixture of 5.67 g of 1-tert-butoxycarbonylmethyl-3-S-amino-2,3,4,5-tetrahydro-1H-(1)-benazepin-2-one and 2.46 g of N-methyl morpholine dissolved in 5 ml methylene chloride at 30 to 35° C. The reaction mixture was further stirred for about 2 hours. The completion of reaction was monitored by HPLC. The reaction was quenched by addition of 40 ml water and 60 ml methylene chloride. The pH was adjusted to 8.5 with 10% aqueous sodium carbonate solution. The organic portion was separated and washed twice with water. It was then dried over anhydrous sodium sulphate and solvent was distilled off to afford (3S)-1-(carboxymethyl-[[(1S)-1-(ethoxycarbonyl)-3-phenylpropyl]amino]-2,3,4,5-tetrahydro-1H-[1]benzazepin-2-one, as an oil.

The oil was dissolved in 50 ml ethylacetate and dry HCl gas was purged at 8-10° C. for few hours to afford benazepril hydrochloride as a fine crystalline slurry. Excess hydrogen chloride was removed by distilling off ethyl acetate in vacuo. The residue was diluted with 45 ml acetone and stirred at 5-8° C. for 1 hour. The product was filtered and dried to constant weight in vacuo at 45-50° C. affording 8.27 gm of almost white product with diastereoisomer ratio of SS:SR= 99.36:0.18, Yield 91.9%.

EXAMPLE 2

Preparation of (3S)-1-(carboxymethyl-[[(1S)-1-(ethoxycarbonyl)-3-phenylpropyl]amino]-2,3,4,5-tetrahydro-1H-[1]benzazepin-2-one Hydrochloride Salt Ethyl(R)-2(trifluoromethane sulphonyloxy)-4-phenylbutyrate (triflate) prepared as mentioned in example 1 to get an oil. The oil was dissolved in 15 ml methylene chloride and a solution of 5.67 g of 1-tert-butoxycarbonylmethyl-3-S-amino-2,3,4,5-tetrahydro-1H (1)-benzazepin-2-one and 2.46 g of N-methyl morpholine in methylene chloride was added dropwise at room temperature. The reaction mixture was stirred for 1 hour. Similar work up as carried out in example 1 afforded benazepril hydrochloride, 8.20 g as almost white powder with diastereoisomer ratio of SS:SR=99.39:0.15, Yield=91.8%.

While the present invention has been described in terms of its specific embodiments, certain modifications and equivalents will be apparent to those skilled in the art and are intended to be included within the scope of the present invention.

We claim:

1. A process for the production of benazepril hydrochloride of Formula (II),

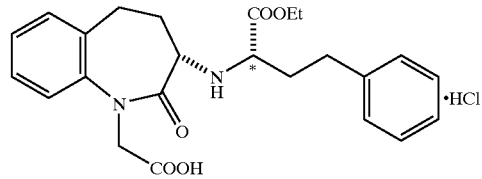

FORMULA II comprising the steps of (i) treating ethyl (R)-2-hydroxy-4-phenylbutyrate of Formula (III)

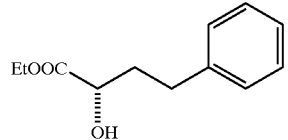

FORMULA III with trifluoromethane sulphonic anhydride of Formula (IV)

$F_3C-SO_2-O-SO_2-CF_3$     FORMULA IV in an inert solvent in the presence of a base and purifying it by passing through a column to obtain trifluoromethane sulfonic ester of ethyl(R)-2-hydroxy-4-phenyl butyrate of Formula (I); and

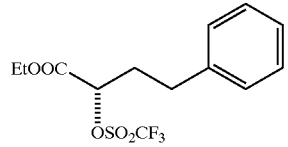

FORMULA I (ii) further condensing said compound of formula I with 1-tert-butoxycarbonylmethyl-3-5-amino-2, 3, 4, 5,-tetrahydro-1H-(1)-enzazepin-2-one of Formula V

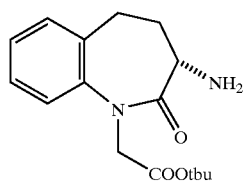

FORMULA V in the presence of an organic solvent and an acid acceptor at a temperature from about 0 to 50° C. for about 1 to 5 hours followed by a suitable work up.

2. The process according to claim 1 wherein the organic solvent is a chlorinated lower alkane.

3. The process according to claim 2 wherein the organic solvent is chloroform or methylene chloride.

4. The process according to claim 1 wherein the acid acceptor is an inorganic base, an organic quaternary ammonium salt, or an organic tertiary base.

* * * * *

UNITED STATES PATENT AND TRADEMARK OFFICE
CERTIFICATE OF CORRECTION

PATENT NO. : 6,919,450 B2
DATED : July 19, 2005
INVENTOR(S) : Thaper et al.

It is certified that error appears in the above-identified patent and that said Letters Patent is hereby corrected as shown below:

Title page,
Item [75], Inventors, "Rajest Kumar Thaper" should read
-- Rajesh Kumar Thaper -- and "Vizianagaram" should read -- Andhra Pradesh --.

Column 1,
Line 42, "Tetrahedron Left" should read -- Tetrahedron Lett. --.
Line 63, "methylpyridine" should read -- methyl pyridine --.

Column 2,
Line 43, "trifluoromethane sulfonating" should read -- trifluoromethanesulfonating --.

Column 3,
Line 8, "benazepin" should read -- benzazepin --.
Lines 27 and 28, "trifluoromethane sulphonic" should read
-- trifluoromethanesulfonic --.

Column 4,
Lines 46 and 54, "trifluoromethane sulphonic" should read
-- trifluoromethanesulfonic --.
Line 67, "enzazepin" should read -- benzazepin --.

Signed and Sealed this

Twenty-eighth Day of February, 2006

JON W. DUDAS
*Director of the United States Patent and Trademark Office*